United States Patent [19]

Mercat

[11] Patent Number: 5,065,633

[45] Date of Patent: Nov. 19, 1991

[54] APPARATUS FOR THE MEASUREMENT OF DRIVE TORQUES

[75] Inventor: Jean-Pierre Mercat, Chateau-Renault, France

[73] Assignee: Look, S.A., Nevers, France

[21] Appl. No.: 507,935

[22] Filed: Apr. 11, 1990

[30] Foreign Application Priority Data

Apr. 19, 1989 [DE] Fed. Rep. of Germany ....... 3912883

[51] Int. Cl.⁵ .............................................. G01L 3/10
[52] U.S. Cl. .................................. 73/862.34; 280/256
[58] Field of Search ........................ 73/862.33, 862.34; 272/73, DIG. 5, DIG. 6; 280/200, 259

[56] References Cited

U.S. PATENT DOCUMENTS 4,811,612  3/1989  Mercat ............................ 73/862.34

FOREIGN PATENT DOCUMENTS 3150149  6/1983  Fed. Rep. of Germany ... 73/862.34
2617970  1/1989  France ............................ 73/862.34

Primary Examiner—Charles A. Ruehl
Attorney, Agent, or Firm—Townsend and Townsend

[57] ABSTRACT

An apparatus for the measurement of the drive torque exerted on a drivable wheel and/or parameters associated therewith in which the measurement parameters are determined in dependence on the relative rotation of two parts disposed in the drive and the relative rotation is mechanically multiplied and increased prior to forming electrical measurement values.

16 Claims, 4 Drawing Sheets

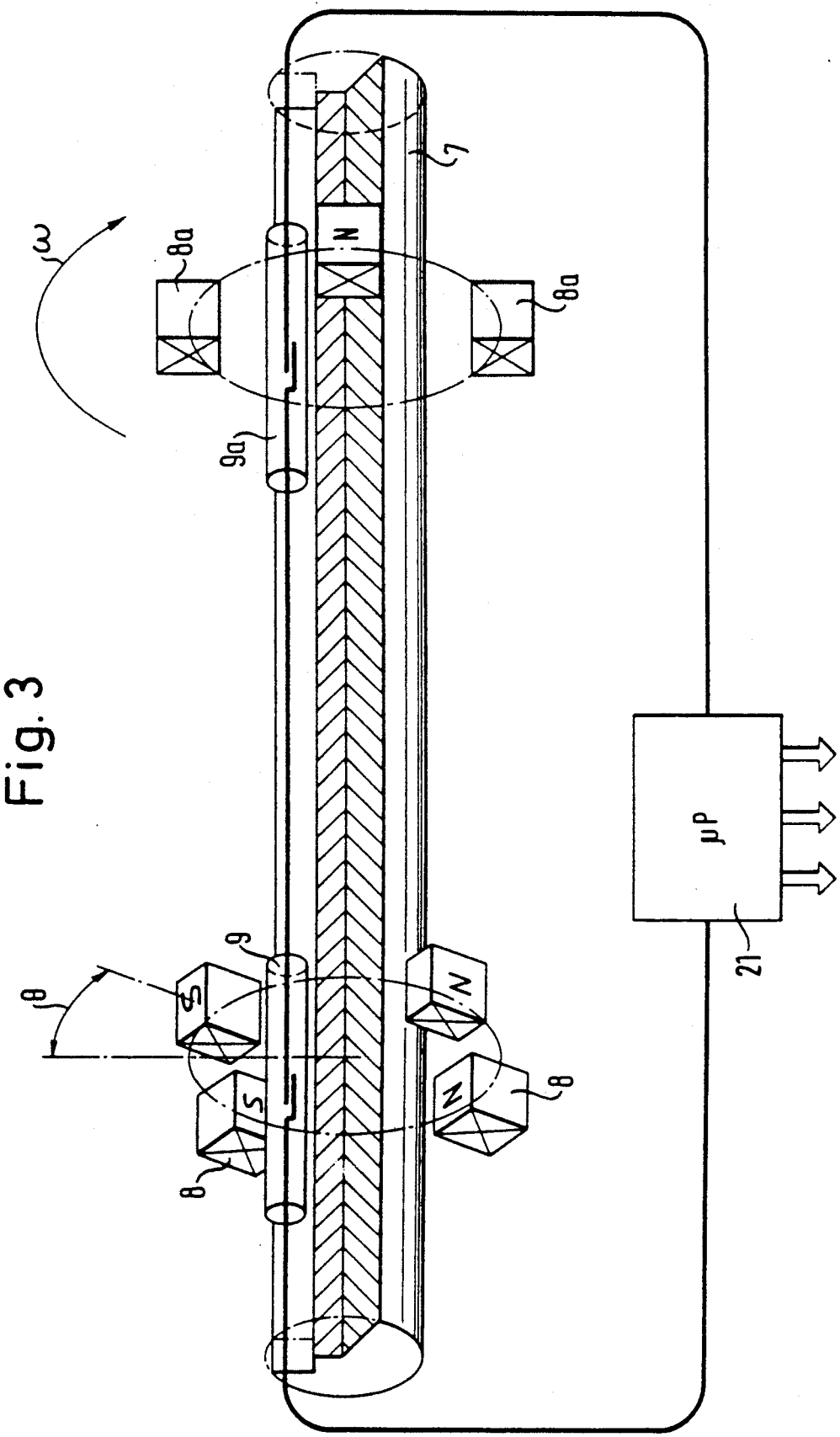

APPARATUS FOR THE MEASUREMENT OF DRIVE TORQUES

BACKGROUND OF THE INVENTION

The invention relates to an apparatus for the measurement of the drive torque exerted on a drivable wheel, in particular on the drive wheel of a bicycle, and/or for the measurement of parameters associated therewith the apparatus being of the kind comprising a wheel hub which is rotatably journalled relative to a fixed axle; a drive axle which is coaxially disposed between the fixed axle and the wheel hub; a member which permits a relative rotation disposed between the drive axle and the wheel hub at the drive side end; a fixed connection formed at the other end between the drive axle and the wheel hub; a device for detecting the relative rotation between the wheel hub and the drive axle which depends on the drive torque and also for generating signals representative of the relative rotation and suitable for evaluation.

For the improvement of physical performance the bicycle is increasingly used in the field of sport as a special training apparatus, and moreover bicycles are increasingly used, in particular in a stationary embodiment, for the treatment and rehabilitation of patients with heart and circulatory illnesses. In carrying out such training and treatment programs it is important to obtain information relative to the power developed by the particular sportsman or patient and the energy consumed, since this information makes it possible to draw conclusions on the training or treatment results.

It is already known from DE-A1 31 50 149 to achieve a largely loss-free power measurement by providing a resilient connection between a driven wheel of a transmission and a component to be driven and to measure the angle of rotation which arises on applying drive forces to the transmission wheel through the relative rotation between the transmission wheel and the component to be driven. Pulse sequences are thereby generated by means of two measurement transducers, with the time separation between the pulses of these measurement transducers being evaluated as a measure for the power which is transmitted. A disadvantage of this known apparatus is above all the fact that the measurement accuracy which can be achieved left much to be desired as result of the difficulty of detecting the very small angle of rotation which amounts to a maximum of 1 to 2 degrees.

SUMMARY OF THE INVENTION

It is accordingly the object of the invention to develop an apparatus of the initially named kind in such a way that the prevailing drive moment and/or parameters associated therewith can be detected extremely precisely in a simple and reliable manner without the occurrence of additional friction effects and over a larger measurement range.

This object is satisfied by an apparatus of the kind set forth, characterized in that a carrier element for at least one measurement transducer is provided in a guide space between the fixed axle and the drive axle and is pivotable about the fixed axle; in that at least one sensor which detects the pivoting of the carrier element is associated with the measurement transducer; and in that the pivot angle of the carrier element is controlled by a mechanical multiplier member which acts between the wheel hub and the drive axle and is actuated by their relative rotation.

Through the provision of a mechanical multiplication the angle of rotation between the drive axle and the wheel hub which depends on the prevailing drive moment is increased substantially, so that the formation of the measurement value via the corresponding sensors can take place with a substantially increased resolution and higher accuracy, so that the actual evaluation results are more reliable.

A pivoted lever is preferably used as the multiplier member and engages in a ring disc-shaped carrier element which is biased by a spring in the direction towards the pivot lever, and this carrier element is pivoted correspondingly multiplied in dependence on the relative rotation between the drive axle and the wheel hub. Thus, the measurement transducers which are held in this carrier element are pivoted over a corresponding angle which can in turn be detected by means of a sensor which is expediently arranged in a recess of the fixed axle.

In accordance with a preferred embodiment of the invention the pivot lever is journalled at one end at an axis fixed relative to the hub, passes through an opening in the drive axle and contacts the pivotable carrier element with its other end. With this arrangement a boundary wall of the opening always contacts the pivot lever as result of the spring bias of the carrier element and thus forms the actual pivot lever actuating member.

As the bearing for the pivot lever is preferably formed in a guide piece fixed relative to the wheel hub, and is arranged directly adjacent the drive axle, even very small relative rotations between the drive axle and the wheel hub already lead to a comparatively large displacement path of the free end of the pivot lever and thus also to a correspondingly large multiplication or transmission ratio.

It is particularly advantageous to form that side surface of the recess in the carrier element which is contacted by the pivot lever, and/or the free end of this pivot lever as a profiled control surface, since in this way the multiplication characteristic can be preset, and in particular it is also possible to obtain a linear translation characteristic.

As measurement transducers or transmitters use is preferably made of several permanent magnets which lie at the same radius and are distributed around the circumference, and reed contacts are provided as the associated sensors. In this way one obtains a simple arrangement which can be realized at favorable cost, which is not liable to break down and which is also space saving. In particularly advantageous manner the measurement transducer can likewise be realized in the form of a resistor, in particular a resistor formed as a surface with an associated tapping element.

Further advantageous developments of the invention are set forth in the subordinate claims.

BRIEF DESCRIPTION OF THE DRAWINGS

The invention will now be described in the following with reference to an embodiment and to the drawings in which are shown.

DESCRIPTION OF THE PREFERRED EMBODIMENTS

Figure 1:
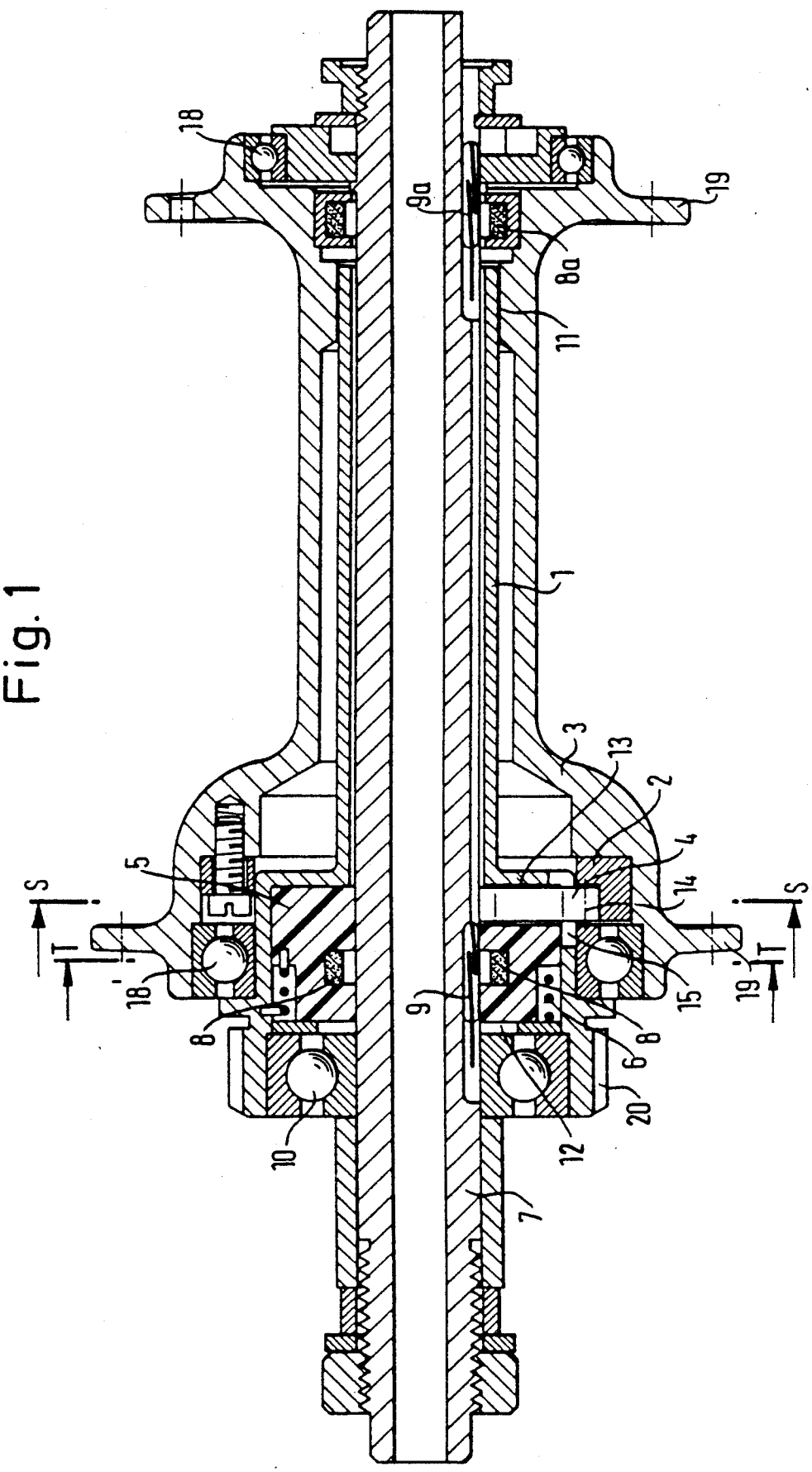
FIG. 1 a schematic axial and sectional representation of a hub unit formed in accordance with the invention for the rear wheel of a bicycle, FIGS. 2a, 2b and 2c sectional illustrations corresponding to the section line S—S in FIG. 1 for various operating states, and FIG. 3 a schematic illustration to explain the arrangement for obtaining and processing signals analogous to the apparatus of FIG. 1, and FIG. 4 a cross-section illustrating a variant and is taken along line T—T in FIG. 1.

FIG. 1 shows a fixed axle 7 for clamping a rear wheel of a bicycle into the forks. On this fixed axle 7 there is rotatably journalled a wheel hub 3 with the usual spoke mounting discs 19 and also a drive axle 1.

The drive axle 1 which is coaxial to the fixed axle 7 is supported at one end via a ball-bearing 10 relative to the fixed axle 7 and is rotationally fixedly connected with the wheel hub 3 at its other end via a fixed connection 11 which is preferably formed by splines.

Figure 4:
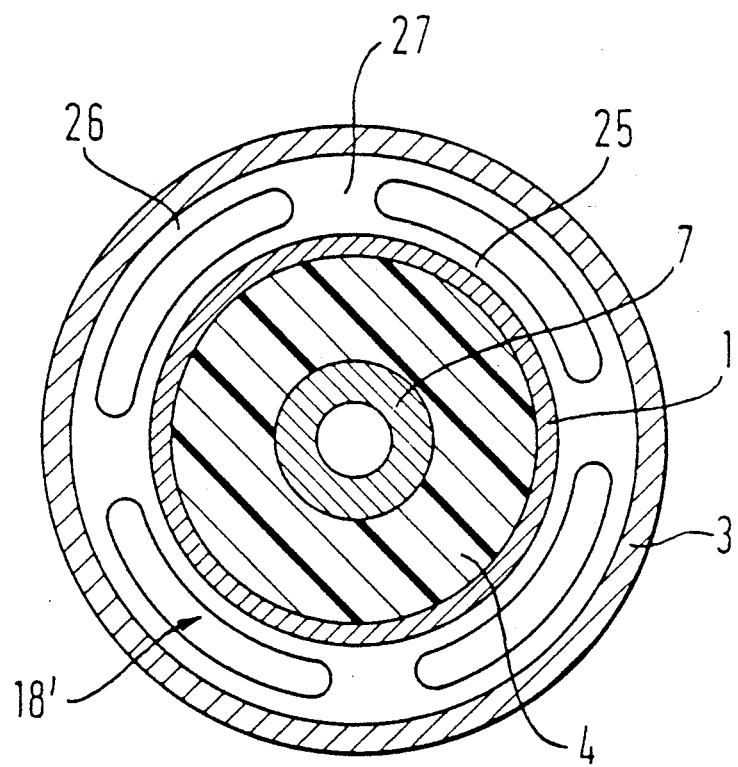

The outwardly disposed free end of the drive axle 1 is provided with a mounting 20 for drive sprocket clusters which are to be secured via a free wheel arrangement. The wheel hub 3 is supported relative to the fixed axle 7 and relative to the outwardly disposed end of the drive axle 1 via ball-bearings 18 and 18' respectively. In place of the ball-bearing 18' at the outwardly disposed end of the drive axle 1 use is preferably made of a double-ring element consisting of plastic, which can be manufactured at particularly favorable cost, in which the two rings 25, 26 acting as support rings are connected together via deformable radial webs 27, as shown in FIG. 4. This one piece element which, from the point of view of its function, fully replaces an expensive ball-bearing permits the required relative rotation without difficulties.

A guide space 12 is formed between the fixed axle 7 and the wheel hub 3, radially inside the ball-bearing 18' provided between the wheel hub 3 and the drive axle, with a ring disc-like carrier element 5 being arranged in this guide space. This carrier element 5 is pivotable about the fixed axle 7 and is biased in one direction by a torsion spring 6. This torsion spring is secured at one end to the carrier element 5 and at its other end to the wheel hub 3. Several permanent magnets 8 which are arranged distributed around the periphery are secured, in particular by adhesive bonding, into corresponding recesses of the carrier element 5 disposed at the fixed axle side.

A guide piece 2 is fixedly connected to the wheel hub 3 and is mounted in the region of the carrier element 5 between the wheel hub 3 and the drive axle. A multiplication element 4 which is formed as a pivoting lever is journalled in the guide piece 2 and is pivotable about an axis 14. This pivotable lever 4 engages into a recess 13 of the carrier element 5.

A reed-contact 9 is arranged opposite to the permanent magnets 8 in the carrier element 5 in a corresponding recess of the fixed axle 7 and this reed-contact switches each time a permanent magnet 8 passes it and generates a pulse having a switching-in flank and a switching-out flank.

A holder for several permanent magnets 8a distributed around the periphery is provided in the wheel hub 3 adjacent the fixed connection 11 between the drive axle 1 and the wheel hub 3, with these permanent magnets 8a being aligned with the permanent magnets 8 provided in the carrier element 5, i.e. being disposed in the same radial planes. A reed-contact 9a fixed in a recess of the fixed axle 7 is also associated with these permanent magnets 8a.

Figure 2A:
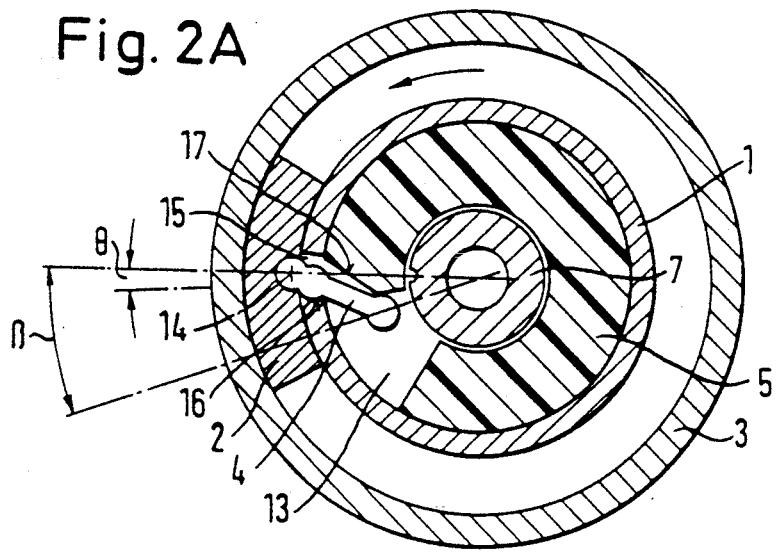

FIG. 2A shows a section corresponding to the section line S—S in FIG. 1, and indeed for the case of a drive moment 0.

The carrier element 5 which is located between the fixed axle 7 and the drive axle 1 is biased in the direction of the arrow by a torsion spring and thus always contacts the pivot lever 4. This pivot lever 4 is pivotally journalled in a matching or fitted recess of the guide piece 2, which is fixedly connected with the wheel hub 3, and extends through an opening 15 of the drive axle 1 into the recess 13 of the carrier element 5 where its free end contacts a profiled control surface 17 of this carrier element 5. Through the spring bias of the carrier element 5 the pivot lever 4 furthermore, always contacts a boundary wall 16 of the opening 15 in the drive axle 1 and this boundary wall 16 forms the actual actuating member for the pivot lever 4.

The distance between the effective point of action of the boundary wall 16 at the pivot lever 4 and the axis 14 fixed relative to the hub is very small and as a consequence very small angles of rotation $\theta$ lead to a larger pivoting angle $\beta$ of the free end of the pivot lever 4 and thus also of the carrier element 5 provided with the permanent magnets 8.

Figure 2B:
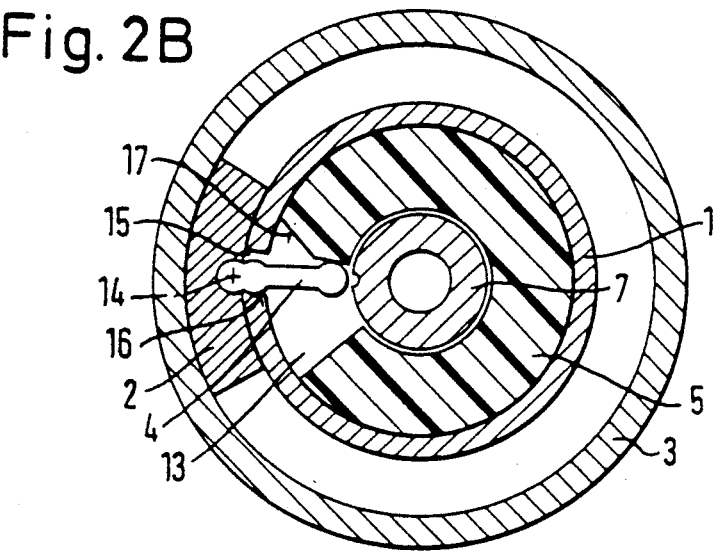

FIG. 2B shows the apparatus with an average torque. Here the pivotal lever 4 has been pivoted as result of a relative rotation between the drive axle 1 and the wheel hub in the counter clock-wise sense and this small relative rotation has led with a corresponding multiplication to a pivotal movement of the carrier element 5 and thus of the permanent magnets secured in this carrier element in the clock-wise sense.

Figure 2C:
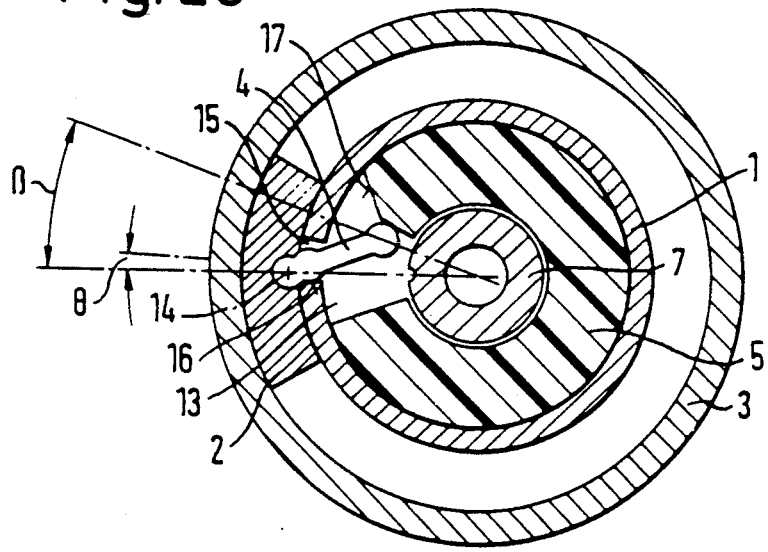

FIG. 2c shows the case of the application of a maximum torque or drive moment. Here a comparison of FIGS. 2A and 2C in particular makes it clear that the mechanical translation of the relative rotation in the drive axle 1 and the wheel hub 3 which depends on the particular drive torque leads to multiplication of this relative rotation which can readily be by factor of from 5 to 10.

By suitable layout of the profiled control surface 17 on the carrier element 5 which cooperates with the pivot lever 4 the respectively desired multiplication characteristic can be preset in a defined manner and can also be selected to be linear.

The schematic representation of FIG. 3 shows the evaluation of the signals obtained with an arrangement of the described kind. The reed contacts 9, 9a which cooperate with the permanent magnets 8, 8a are connected electrically in series. If no drive torque is exerted on a wheel provided with the apparatus of the invention then the pulse sequences generated by the reed contacts 9, 9a are in phase. If a drive torque is applied to the drive axle then an angular displacement results between the magnets 8, 8a which rotate with the same angular speed $\omega$ and thus also a displacement of the switching-in and switching-out flanks of the pulses generated by the reed contact 9 relative to the corresponding flanks of the pulses generated by the reed contact 9a and brought about by the fixedly mounted magnets 8a. The evaluation of these pulse sequences preferably takes place by means of a microprocessor 21 which also makes it possible to form the drive torques and/or parameters associated therewith by processing of the signals that are obtained, which is indicated by the output arrows associated with the microprocessor 21.

I claim:

1. Apparatus for the measurement of the drive torque exerted on a drivable wheel, in particular on the drive wheel of a bicycle, and/or of parameters associated with the drive torque, the apparatus comprising a wheel hub (3) which is rotatably journalled relative to a fixed axle (7); a drive axle (1) which is coaxially disposed between the fixed axle (7) and the wheel hub (3); a member (18') which permits a relative rotation disposed between the drive axle (1) and the wheel hub (3) at the drive side end; a fixed connection (11) formed at the other end between the drive axle (1) and the wheel hub (3); a device for detecting the relative rotation between the wheel hub (3) and the drive axle (1) which depends on the drive torque and also for generating signals representative of the relative rotation and suitable for evaluation, characterized in that a carrier element (5) for at least one measurement transducer (8) is provided in a guide space (12) between the fixed axle (7) and the drive axle (1) and is pivotable about the fixed axle (7); in that at least one sensor (9) which detects the pivoting of the carrier element (5) is associated with the measurement transducer (8); and in that the pivot angle of the carrier element (5) is controlled by a mechanical multiplier member (4) which acts between the wheel hub (3) and the drive axle (1) and is actuated by their relative rotation.

2. Apparatus in accordance with claim 1, characterized in that the sensor is fixed relative to the fixed axle (7), the drive axle (1) or the hub (3).

3. Apparatus in accordance with claim 1, characterized in that at least one further pair comprising a measurement transducer (8a) and associated sensor (9a) is provided outside of the region of the drive axle (1) at the wheel hub (3) or at the fixed axle (7).

4. Apparatus in accordance with claim 3, characterized in that at least one measurement transducer (8a) comprises a permanent magnet and that at least one sensor (9a) comprises read contacts.

5. Apparatus in accordance with claim 1, characterized in that the guide space (12) for the pivotable carrier element (5) is provided in the region of the drive side end of the drive axle (1), and in particular radially inside the member (18') which is provided between the wheel hub (3) and the drive axle (1) and which permits a relative rotation.

6. Apparatus in accordance with claim 1, characterized in that the member (18') which permits a relative rotation comprises either an arrangement of two concentric plastic rings which are connected together by deformable radial webs or a ball-bearing.

7. Apparatus in accordance with claim 1, characterized in that the pivotable carrier element (5) is of ring disc-like shape and is biased by a spring (6) in a direction towards the multiplier member (4).

8. Apparatus in accordance with claim 7, characterized in that the ring disc-like carrier (5) has a recess (13), and that the multiplier member (4) is formed as a pivot lever engaged by the wall of said recess.

9. Apparatus in accordance with claim 8, characterized in that the pivot lever (4) is journalled at one end at an axis (14) fixed relative to the hub, passes through an opening (15) in the drive axle (1) and contacts the carrier element (5) with its free end; and in that a boundary wall (16) of the opening (15) always contacts the pivot lever (4) as a result of the spring bias of the carrier element (5) and forms an actuating member for the pivot lever.

10. Apparatus in accordance with claim 9, characterized in that the axis (14) for the pivot lever (4) is formed as a bearing provided in a guide piece (2) which is fixedly connected to the wheel hub (3) and is arranged directly adjacent the drive axle 1.

11. Apparatus in accordance with claim 8, characterized in that the wall of said recess (13) in the carrier element (5) engaged by the pivot lever (4) has a side surface formed as a profiled control surface (17).

12. Apparatus in accordance with claim 11, characterized in that the profiled control surface (17) is so laid out that a linear multiplication characteristic is present.

13. Apparatus in accordance with claim 11, characterized in that the free end of the pivot lever (4) has a shape which corresponds to a contour of the control surface.

14. Apparatus in accordance with claim 1, characterized in that the carrier element (5) consists of plastic.

15. Apparatus in accordance with claim 1, characterized in that at least one measurement transducer (8) comprises a permanent magnet and that at least one sensor (9) comprises reed contacts.

16. Apparatus in accordance with claim 15, characterized in that signals associated with the opening and closing of the reed contacts (9, 9a) have flanks whose timewise displacement is used as the measurement parameter representative of the particular drive torque.

* * * * *